United States Patent
Stolikj et al.

(10) Patent No.: US 12,259,801 B2
(45) Date of Patent: Mar. 25, 2025

(54) SYSTEM AND METHOD FOR AUTOMATED OR SEMI-AUTOMATED IDENTIFICATION OF MALFUNCTION AREA(S) FOR MAINTENANCE CASES

(71) Applicant: KONINKLIJKE PHILIPS N.V., Eindhoven (NL)

(72) Inventors: Milosh Stolikj, Eindhoven (NL); Qi Gao, Eindhoven (NL); Bart Albertus Gerardus Van Der Velden, Eindhoven (NL); Jurgen Jan Rusch, Eindhoven (NL); Eugene Alekseyevich Ivanov, Eindhoven (NL); Mauro Barbieri, Eindhoven (NL); Johannes Henricus Maria Korst, Eindhoven (NL); Marc André Peters, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 31 days.

(21) Appl. No.: 18/036,179

(22) PCT Filed: Nov. 10, 2021

(86) PCT No.: PCT/EP2021/081178
§ 371 (c)(1),
(2) Date: May 10, 2023

(87) PCT Pub. No.: WO2022/101234
PCT Pub. Date: May 19, 2022

(65) Prior Publication Data
US 2023/0418721 A1    Dec. 28, 2023

Related U.S. Application Data

(60) Provisional application No. 63/113,208, filed on Nov. 13, 2020.

(51) Int. Cl.
G06F 11/32    (2006.01)
G06F 11/22    (2006.01)
G16H 40/40    (2018.01)

(52) U.S. Cl.
CPC ........ G06F 11/321 (2013.01); G06F 11/2268 (2013.01); G16H 40/40 (2018.01)

(58) Field of Classification Search
CPC ... G06F 11/321; G06F 11/2268; G16H 40/40; G05B 23/0272
(Continued)

(56) References Cited

U.S. PATENT DOCUMENTS

| | | |
|---|---|---|
| 7,069,333 B1 | 6/2006 | Morris |
| 2004/0138920 A1 | 7/2004 | Sawanaga |

(Continued)

FOREIGN PATENT DOCUMENTS

| | | |
|---|---|---|
| WO | 2019/243291 A1 | 12/2019 |
| WO | 2022/018104 A1 | 1/2022 |

OTHER PUBLICATIONS

International Search Report and Written Opinion Dated Mar. 4, 2022 For International Application No. PCT/EP2021/081178 Filed Nov. 10, 2021.

*Primary Examiner* — Yair Leibovich

(57) ABSTRACT

A method (100) of automated identification of one or more malfunction areas of a set (S) of malfunction areas for a service case in which a medical device (12) is serviced includes: generating an output probability vector (40) of probabilities for the set of malfunction areas of the medical device by operations including applying at least one classifier (42, 46) to at least one of (1) text descriptions of parts ordered for the service case and/or (2) a text description of the service case; and displaying a list (56) of one or more most probable malfunction areas for the service case wherein the one or more most probable malfunction areas (Continued)

are the one or more most malfunction areas of the set of malfunction areas having highest probability in the output probability vector.

20 Claims, 3 Drawing Sheets

(58) Field of Classification Search
USPC .......................................................... 714/46
See application file for complete search history.

(56) References Cited

U.S. PATENT DOCUMENTS

2019/0080072 A1* 3/2019 Van Os .................. G06F 3/016
2020/0134574 A1 4/2020 Ghosh

* cited by examiner

SYSTEM AND METHOD FOR AUTOMATED OR SEMI-AUTOMATED IDENTIFICATION OF MALFUNCTION AREA(S) FOR MAINTENANCE CASES

CROSS REFERENCE TO RELATED APPLICATIONS

This application is the U.S. National Phase application under 35 U.S.C. § 371 of International Application No. PCT/EP2021/081178 filed Nov. 10, 2021, which claims the benefit of U.S. Provisional Patent Application No. 63/113,208 filed Nov. 13, 2020. These applications are hereby incorporated by reference herein.

FIELD

The following relates generally to the maintenance arts, medical device arts, medical device maintenance arts, probability vector generation arts, and related arts.

BACKGROUND

A medical imaging system may occasionally malfunction. In such situations, a service case is created, which captures all maintenance activities carried out to diagnose and resolve the issue. A malfunction area of the service case is defined as the subcomponent or functional subsystem of the medical imaging system which failed to work as. It is used both for diagnostic purposes, as well as for reliability analysis.

Typically, the list of possible malfunction areas is created and maintained by domain experts. In some approaches, the malfunction areas can be determined based on a particular maintenance activity performed during the service case. Each maintenance activity is manually assigned to a malfunction area, and a malfunction area of the service case is determined by applying fixed rules to the set of (maintenance activities, malfunction area) pairs. An example of such an approach is to determine a malfunction area of the service case based on the replaced parts in the service case. For that approach, a mapping between parts and malfunction areas is maintained. An example of a rule for determining a malfunction area of the service case is to use the functional subsystem of the most expensive replaced part.

In other examples, the malfunction areas can be determined based on pre-defined text patterns/regular expressions for service actions, which are mapped to malfunction areas. An example of such an approach would be to assign malfunction areas to error codes found in machine logs. Then, if an error code appears anywhere in a service case (e.g. in the log data, or in engineering notes), the appropriate malfunction area is used for the service case.

Both approaches require significant effort from experts to maintain the mapping between maintenance activities (e.g. based on replaced parts) or patterns (e.g. based on encountered error codes) and malfunction areas. For instance, for one Magnetic Resonance Imaging (MRI) scanner design, more than 10,000 different parts are in use, and more than 45,000 unique three-word combinations are found in engineering notes in historical service cases (word combinations that appear in at least 5% and at most in 70% in the cases). Manually processing and maintaining such a list is a labor-intensive operation. Furthermore, it is often not clear which malfunction area should be assigned to a part since the same part may be used for resolving different issues (e.g. replacement kits).

Furthermore, both approaches identify a malfunction area retrospectively. This is because the part replaced, or the service action entries, are not available in complete form until after the service case is closed.

The following discloses certain improvements to overcome these problems and others.

SUMMARY

In one aspect, a non-transitory computer readable medium stores instructions executable by at least one electronic processor to perform a method of automated identification of one or more malfunction areas of a set of malfunction areas for a service case in which a medical device is serviced. The method includes: providing a parts ordering user interface for ordering parts for the service case, the parts ordering user interface providing text descriptions of the parts ordered for the service case; providing a service report entry user interface for receiving a text description of the service case including at least a malfunction report for the medical device and repair notes for the service case; generating an output probability vector of probabilities for the set of malfunction areas of the medical device by operations including applying at least one classifier to at least one of (1) the text descriptions of the parts ordered for the service case and/or (2) the text description of the service case; and displaying a list of one or more most probable malfunction areas for the service case wherein the one or more most probable malfunction areas are the one or more most malfunction areas of the set of malfunction areas having highest probability in the output probability vector.

In another aspect, an apparatus for automated identification of one or more malfunction areas of a set of malfunction areas for a service case in which a medical device is serviced includes a server computer. A non-transitory computer readable medium stores instructions executable by the server computer to perform a method including: providing a parts ordering user interface for ordering parts for the service case, the parts ordering user interface providing text descriptions of the parts ordered for the service case; providing a service report entry user interface for receiving a text description of the service case including at least a malfunction report for the medical device and repair notes for the service case; generating a first probability vector of probabilities for the set of malfunction areas of the medical device by applying a first classifier to the text descriptions of the parts ordered for the service case; generating a second probability vector of probabilities for the set of malfunction areas of the medical device by applying a second classifier to the text description of the service case; combining the first probability vector and the second probability vector to generate an output probability vector of probabilities of the one or more malfunction areas of the medical device; and displaying a list of one or more most probable malfunction areas for the service case wherein the one or more most probable malfunction areas are the one or more most malfunction areas of the set of malfunction areas having highest probability in the output probability vector.

In another aspect, a method of automated identification of one or more malfunction areas of a set of malfunction areas for a service case in which a medical device is serviced includes: providing a parts ordering user interface for ordering parts for the service case, the parts ordering user interface providing text descriptions of the parts ordered for the service case; providing a service report entry user interface for receiving a text description of the service case including at least a malfunction report for the medical device and repair notes for the service case; generating an output probability vector of probabilities for the set of malfunction areas of the medical device by operations including applying at least one classifier to at least one of (1) the text descriptions of the parts ordered for the service case and/or (2) the text description of the service case; displaying a list of one or more most probable malfunction areas for the service case wherein the one or more most probable malfunction areas are the one or more most malfunction areas of the set of malfunction areas having highest probability in the output probability vector; receiving a user-identified malfunction area for the service case via a user input device interacting with the displayed list; and automatically adding the user-identified malfunction area to the text description of the service case.

One advantage resides in reducing downtime of a medical imaging device.

Another advantage resides in automatically identifying one or more proposed malfunction areas of a medical device based on interaction of the service technician with existing systems such as a parts ordering user interface and/or a service report entry user interface.

Another advantage resides in generating patterns from historical cases to determine potential malfunction areas of a medical device.

Another advantage resides in providing one or more proposed malfunction areas during execution of a service call, thereby providing this information in real time for consideration by the service technician in deciding how to perform the servicing.

Another advantage resides in recommending repair actions for one or more potential malfunction areas of a medical device.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
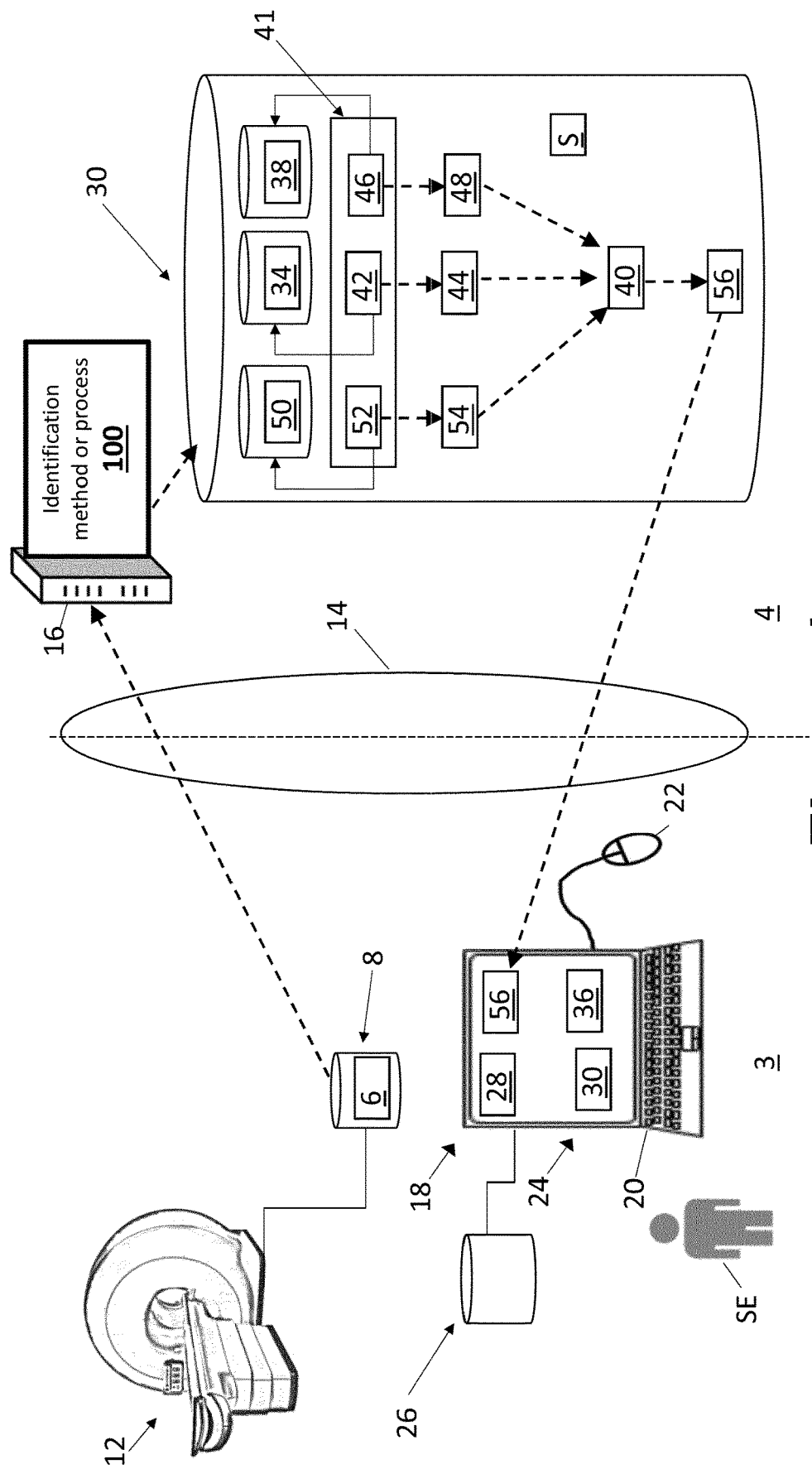
FIG. 1 diagrammatically illustrates an illustrative system for generating a ranked list of alerts from logs files of medical electronic devices in accordance with the present disclosure.

Current methods of servicing medical devices include identifying a malfunction area associated with each service call. By way of non-limiting illustrative example, one medical imaging device manufacturer currently defines 13 malfunction areas for a magnetic resonance imaging (MRI) scanner, including, for example: RF coils, patient support, RF (amplifiers et cetera), gradient coils, image quality, data acquisition and so forth. A given malfunction may fit into multiple malfunction areas, for example a problem with an RF coil may impact the RF coils, image quality, and data acquisition malfunction areas. In such an "overlapping" case, the usual practice is to assign a single most relevant malfunction area for the case. (in this example, the "RF coils" malfunction area would most likely be assigned as the problem directly relates to the RF coils).

Presently, a malfunction area is assigned to a service case retrospectively, that is, at or after closing the case. A malfunction area may be assigned automatically based on the major replaced part, or manually by the service technician. For the former approach, malfunction areas are assigned to replacement parts during MRI system design, or the first time the part is replaced and the service engineer assigns a malfunction area to that part then thereafter the same malfunction area is assigned to that part.

However, there are some difficulties with this approach. It may not be apparent which is the "major part" that was replaced in a service call. For example, the service engineer may replace a low-cost part to solve the actual malfunction, but during the service call may also perform preventive maintenance involving replacing a higher-cost part, thereby creating a misassignment of a malfunction area based on the higher-cost part that was not implicated in the actual malfunction.

Furthermore, the assignment of malfunction area retrospectively has the disadvantage of not providing the service engineer with real-time information. Knowing the (most likely) malfunction area during servicing could be useful information for the service engineer.

In view of the foregoing, the following discloses an approach for dynamic likely malfunction area assignment. In the illustrative examples, two data sources are mined: the part descriptions of replaced parts and written notes including the malfunction report and notes generated by the service engineer during the servicing. However, it is contemplated to use only one of these data sources. Conversely, other sources are also contemplated to be mined, such as machine logs. The illustrative example creates and utilizes three classifiers for determining the probable malfunction area(s), as follows.

A first classifier receives as input a bag-of-words representation of the parts descriptions for the part or parts ordered for replacement, and outputs a (first) vector of probabilities of the malfunction areas based on those parts descriptions. For example, if MRI has 13 malfunction areas then the output vector has 13 elements corresponding to the respective malfunction areas. If the first vector element corresponds to the 'RF coils' malfunction area then the value of the first vector element stores the probability that a malfunction area for the service case is 'RF coils'; if the second vector element corresponds to the patient support malfunction area then the value of the second vector element stores the probability that a malfunction area for the service case is patient support; and so forth.

A second classifier receives as input a bag-of-words representation of the malfunction report and service engineer notes and operates similarly to the first classifier to output a second vector of probabilities of the malfunction areas, with this vector being based on the text description of the service case.

The first and second classifiers can be any text classifier, such as, by way of non-limiting illustrative example, a support vector machine (SVM) classifier.

A third classifier combines the outputs of the first and second classifiers. Hence, the third classifier receives the first and second vectors of probabilities output by the first and second classifiers, and outputs a vector of probabilities of the malfunction areas. The third classifier can employ averaging, majority voting, linear regression, decision trees, or other approaches for combining the results.

The three classifiers are trained on a training set of historical service cases that have already been annotated by experts with malfunction area.

The trained classifiers may be used as follows. The service engineer accesses the usual service case application via which the service engineer receives the malfunction report, interfaces with a parts ordering system to order parts, enters the service engineer notes, and may engage in other activities such as bringing up and following a root cause isolation flowchart or decision tree or utilize other diagnostic tools. A malfunction area module as disclosed herein is also included in the service case application. This module runs in the background, and receives the malfunction report, parts descriptions of ordered parts (such a part description is automatically provided by the parts ordering user interface when the user selects a part for order), and entered service engineer notes in real time. As these activities are received, the textual information (e.g. textual part descriptions and textual service engineer notes) is extracted and run through the appropriate classifiers to generate a ranked list of most likely malfunction areas. As these are fast operations, the output of any classifier and hence the ranked list is updated in (near) real-time. A window of the service case application displays the most likely malfunction area, or in a preferred approach, a "top-N" most likely malfunction areas. The use of a specific classifier is dependent on the status of the problem resolution. If the service engineer has not resolved the problem, then the list of ordered part is empty, and the first and third classifiers cannot be run. Therefore, in this case, only the second classifier is used to produce a ranked list of most likely malfunction areas. This list can be used by the service engineer to guide him during root cause analysis. If the service engineer has resolved the problem, then the output of all three classifiers is considered, and the output from the third classifier (i.e. the combined vector of probabilities of the malfunction areas) is used to produce a ranked list of most likely malfunction areas While described in the context of MRI in the illustrative examples, the approach is also suitably used for servicing of any imaging modality, such as X-ray, Computed Tomography (CT), Positron Emission Tomography (PET), Single Photon Emission Computed tomography (SPECT), Ultrasound, and so forth. In addition, the approach can be used for other medical devices, such as patient monitors.

With reference to FIG. 1, an apparatus or system 10 for automated identification of one or more malfunction areas of a set S of malfunction areas for a service case in which a medical device 12 is serviced is shown. As shown in FIG. 1, a service engineer SE, who is servicing a medical imaging device (also referred to as an image acquisition device, imaging device, and so forth) 2, is located in a medical imaging device bay 3, and a server computer 16 is disposed in a remote service location or center 4. The remote location 4 is typically a site owned or leased or otherwise controlled by the imaging device vendor or other imaging device service provider.

A single image acquisition device 12 is shown by way of illustration, which can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 12 may also be a hybrid imaging device such as a PET/CT or SPECT/CT imaging system. While a single image acquisition device 12 is shown by way of illustration in FIG. 1, more typically the service location or center 4 will provide monitoring and maintenance servicing for a fleet of imaging devices, e.g. for all or a subset of medical imaging devices sold by the vendor under service contracts between the customers (e.g., owner or operator of the imaging bays 3).

In a typical scenario, the imaging device 12 automatically generates machine logs that record operational information pertaining to the imaging devices 12, such as scans performed, hardware and parameters used in the scans, device configuration changes, and so forth. These logs can be automatically transferred to the service center 4 by way of the communication link 14, such as the Internet possibly augmented by local area networks at the customer end 3 and/or at the service center end 4. These logs may for example be transferred on a daily basis or more or less frequently.

FIG. 1 also shows the service engineer SE operating a service device 18, which comprises an electronic processing device such as a smartphone, a tablet, a laptop computer, or more generally a computer. The service device 18 includes typical components, such as an electronic processor 20 (e.g., a microprocessor), at least one user input device (e.g., a mouse, a keyboard, a trackball, a touch screen, and/or the like) 22, and at least one display device 24 (e.g. an LCD display, plasma display, cathode ray tube display, and/or so forth). The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the service device 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the service device display device 24.

The disclosed communication link 14 includes the server computer 16 (or a cluster of servers, cloud computing resource comprising servers, or so forth) which is programmed to establish connections between the server computer and the service engineer SE.

The server computer 16 is operatively connected with a one or more non-transitory storage media 30. The non-transitory storage media 30 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the server computer 16, various combinations thereof, or so forth. It is to be understood that any reference to a non-transitory medium or media 30 herein is to be broadly construed as encompassing a single medium or multiple media of the same or different types. Likewise, the server computer 16 may be embodied as a single electronic processor or as two or more electronic processors. The non-transitory storage media 30 stores instructions executable by the server computer 16.

Furthermore, as disclosed herein the server computer 16 performs a method or process 100 for automated identification of one or more malfunction areas of a set S of potential malfunction areas for a service case in which the medical device 12 is serviced. The set S of potential malfunction areas can be stored in the non-transitory storage media 30 of the server computer. The non-transitory storage media 30 also stores instructions for the server computer 16 to perform the method 100.

Figure 2:
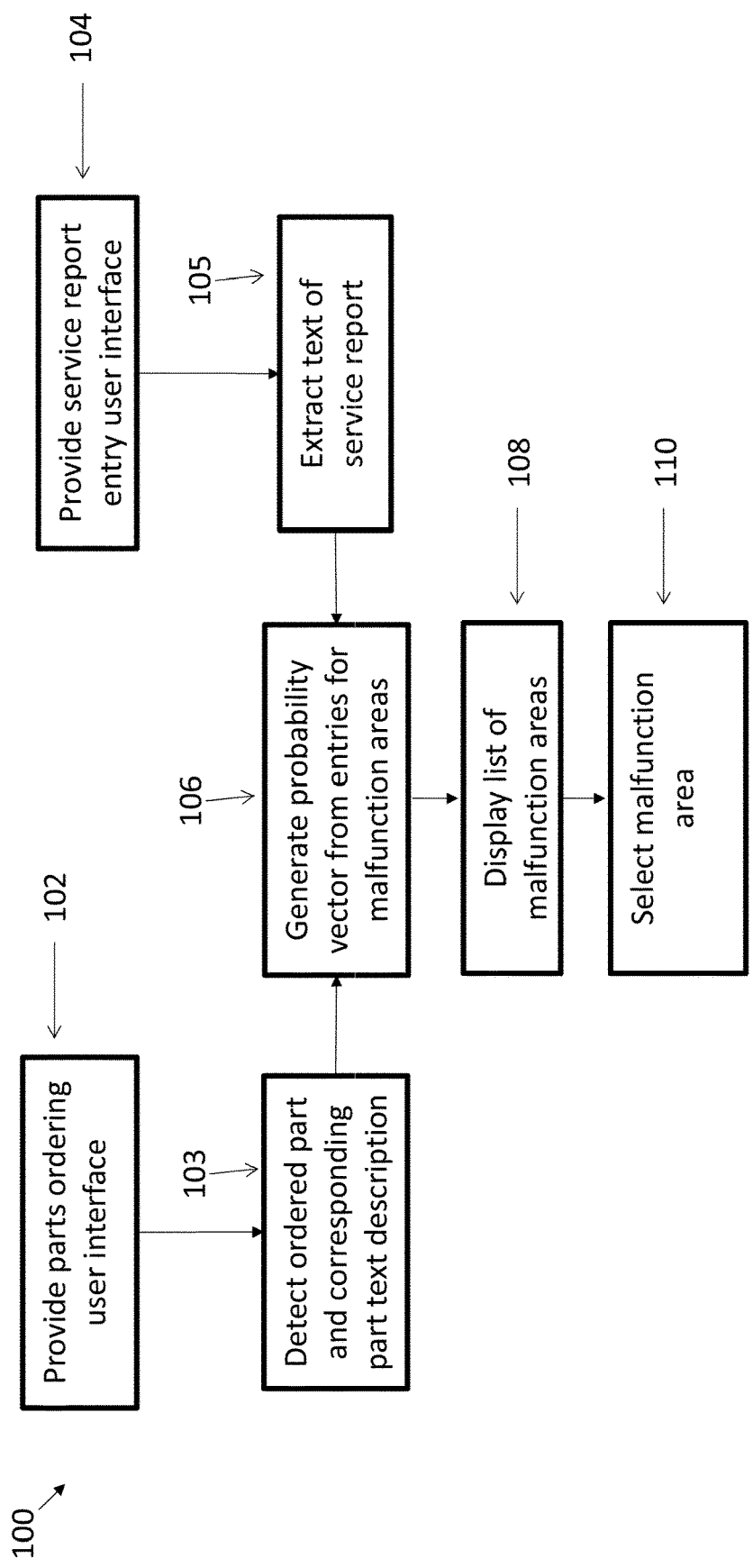
FIG. 2 shows exemplary flow chart operations of the system of FIG. 1.

With reference to FIG. 2, and with continuing reference to FIG. 1, the method 100 is shown as an exemplary flow chart. In some examples, the method 100 may be performed at least in part by cloud processing. To begin the method 100, the service engineer SE begins a service case to service the medical device 12 and logs on to the service device 18 to connect the service device 18 to the server computer 16 via the communication link 14.

At an operation 102, a parts ordering user interface 32 for ordering parts for the service case is provided on the GUI 28 of the service device 18. The parts ordering user interface 32 provides text descriptions of the parts ordered for the service case. The service engineer SE can order a part via the user input device 22 (e.g., by tapping on the screen of the service device 18, or with mouse clicks or keyboard strokes via a mouse of keyboard comprising the at least one user input device). When this occurs, the parts ordering user interface 32 retrieves a text description of the ordered part from a first database 34 of the non-transitory computer readable medium 30 of the server computer 16. The parts ordering user interface 32 provides for ordering parts for the service case from a parts inventory, which can include, for example, at least 8000 parts. In some examples, none of the text descriptions of the at least 8000 parts of the parts inventory include annotations indicating malfunction areas associated to the parts.

The server computer 16 also includes a malfunction area module 41 that is also included in the service case application. The malfunction area module 41 runs in the background, and receives the malfunction report, parts descriptions of ordered parts (such a part description is automatically provided by the parts ordering user interface 32 when the user selects a part for order), and entered service engineer notes in real time.

At an operation 103 performed by the malfunction area module 41, the ordered part is detected, and the corresponding part description is extracted. This can be done using a suitable application programming interface (API) or other hook enabling the malfunction area module to receive this information. The extracted part description is preferably converted to a standardized format suitable for input to a text classifier. For example, the part description can be converted to a bag-of-words representation, optionally with other processing such as removing frequent and uninformative "stop" words (e.g., "and", "the", et cetera).

At an operation 104 (which may in general be performed before, after, or concurrently with, operation 102), a service report entry user interface 36 for receiving a text description of the service case is provided on the GUI 28 of the service device 18. The service report entry user interface 36 can include at least a malfunction report for the medical device 12 and repair notes for the service case. This malfunction report would typically be entered by an imaging technician or other user of the MRI 12 and would typically have been uploaded to the server computer 16 and subsequently downloaded to the service device 18 when the SE opened the service case. The service engineer SE can input repair notes via the user input device 22 (e.g., by tapping on the screen of the service device 18, or with mouse clicks or keyboard strokes via a mouse of keyboard comprising the at least one user input device), and this information would also be included in the developing service report. The written notes can be stored in a second database 38 of the non-transitory computer readable medium 30 of the server computer 16.

At an operation 105 performed by the malfunction area module 41, the text content of the developing service report is extracted, preferably in (near) real-time, e.g. as the text is entered into the service report entry user interface 36. This can again be done using a suitable API or other hook enabling the malfunction area module to receive this information. The extracted text is preferably converted to a standardized format suitable for input to a text classifier. For example, the text can be converted to a bag-of-words representation, optionally with other processing such as removing frequent and uninformative "stop" words (e.g., "and", "the", et cetera).

At an operation 106, an output probability vector 40 of probabilities for the set S of malfunction areas of the medical device 12 is generated by operations including applying at least one classifier to at least one of (1) the text descriptions of the parts ordered for the service case and/or (2) the text description of the service case. The vector generation operation 106 can be performed in a variety of manners.

In some embodiments, the vector generation operation 106 includes applying a first classifier 42 to the text descriptions of the parts ordered for the service case. To do so, the first classifier 42 can mine the first database 34 to find the text descriptions for the service case. From the retrieved data, the first classifier 42 is programmed to output a first probability vector 44 for the set S of malfunction areas of the medical device 12.

In other embodiments, the vector generation operation 106 includes applying a second classifier 46 to the to the text description of the service case. To do so, the second classifier 46 can mine the second database 38 to find the to the text descriptions for the service case. From the retrieved data, the second classifier 46 is programmed to output a second probability vector 48 for the set S of malfunction areas of the medical device 12.

In further embodiments, the first probability vector 44 and the second probability vector 48 are both generated, and then are combined to generate the output probability vector 40 of probabilities for the set S of malfunction areas of the medical device 12. In some examples, the first classifier 42 and/or the second classifier 46 can be a support vector machine (SVM) classifier.

In still further embodiments, the medical device 12 can store log files 6 in a non-transitory computer readable medium 8 of the medical device. The log files 6 can be automatically maintained and can be transmitted to the server computer 6 and stored in a third database 50. A third classifier 52 can mine the third database 50 to find the log files 6 and generate a third probability vector 54 therefrom. The output probability vector 40 can be generated from a combination of the first probability vector 44, the second probability vector 48, and the third probability vector 54. Although not utilized in the illustrative examples, it is contemplated for such machine log data to be mined as a third data source. In such embodiments, the third classifier 52 comprises an additional text-based classifier would ingest the machine log text and output a vector of probabilities for the set S of malfunction areas of the medical device 12. This could then be combined by the third classifier along with the illustrative first and second vectors of 44, 48 probabilities output by the illustrative first and second text classifiers 42, 46. The additional use of the machine log data would be expected to provide (even) more accurate probable malfunction areas.

At an operation 108, a list 56 of one or more most probable malfunction areas for the service case is displayed on the display device 24 of the service device 18. The one or more most probable malfunction areas are the one or more most malfunction areas of the set S of malfunction areas having highest probability in the output probability vector 40. In some examples, the list 56 can comprise a top "N" number of malfunction areas can be included in the list. It is also contemplated for the list to have only a single most probable malfunction area (equivalent to a top-N list where N=1). In another approach, the number of listed malfunction areas is not preset, but rather each malfunction area whose probability exceeds some predefined threshold (e.g. probability of 0.75 or higher) is included in the list.

As noted, the output probability vector 40 represents of probabilities for the set S of malfunction areas of the medical device 12. Each probability of probabilities of the one or more malfunction areas of the medical device 12 can correspond to a corresponding potential malfunction of the medical device The set S of malfunction areas a single malfunction area of the medical device 12; however, the output probability vector 40 is representative of the entire set S of malfunction areas, so that the service engineer SE can select one of the malfunction areas from the set of malfunction areas.

In some embodiments, the displaying operation 108 can include receiving a selection of a user-identified malfunction area for the service case via the user input device 22 interacting with the displayed list 56. For example, the service engineer SE can select a malfunction area on the display device 24 with a finger tap or with mouse clicks or keyboard strokes via a mouse of keyboard comprising the at least one user input device). The selected user-identified malfunction area can be automatically added to the text description of the service case.

In some embodiments, the generating operation 106 of the output probability vector 40 and the displaying operation 108 of the list 56 are repeated iteratively (for example, each time one of the extraction operations 103, 105) detects new information in the form of a newly ordered part with corresponding part description per operation 103 or text added to the developing service call report per operation 105) to update the list in real-time as the parts ordering user interface 32 receives orders for parts for the service case and/or the service report entry user interface 36 receives updated repair notes for the service case.

At an operation 110, the service engineer SE can select a final determination of the malfunction areas, which is then included in the report. The report can be stored in the non-transitory computer readable medium 30 of the server computer 16. In some examples, a recommended repair action for the service case can be displayed on the display device 24.

EXAMPLE

The following describes in more detail the algorithms of the method 100. The method 100 aims to make the process of identifying malfunction areas more efficient, by using the apparatus 10 for automatic identification of the malfunction areas for new service cases. The databases 34, 38, 50 are built by learning patterns from historical service cases, which have already been annotated with the appropriate malfunction areas. The maintenance activities in each service case are treated as textual fields, and the words and sequences of words (e.g. three-word combinations) in each activity are used as initial features. Then, several text classifiers 44, 48, 54 are built, focusing on particular maintenance activities (e.g. using only descriptions of replaced parts as features), or on all activities in a service case. The output probability vector 40 of all these classifiers 44, 48, 54 may be combined (i.e. used as features for a subsequent classifier), to give a more precise prediction of the malfunctioning area of each service case.

These learned patterns do not have to be reviewed by an expert. Typically, the expert is required for occasional quality control of the automated system. This significantly reduces their workload, as a small fraction of the new service cases would need to be inspected.

Furthermore, the method 100 can be used to classify both closed service cases and open service cases, which are still being handled by the service engineer SE. In the former case, the apparatus 10 can use all recorded activities in a service case to determine the malfunction areas. In the latter case, since the service case is ongoing, only a subset of the maintenance activities has been completed and registered. The apparatus 10 would use only this information and can produce the list 56 of likely malfunction areas. The service engineer SE can use this list 56 to narrow down the problem area and identify the root-cause more efficiently (FIG. 4). The service engineer SE can use the apparatus 10 multiple times during the handling of a service case (e.g. after each diagnostic step has been performed), to produce an updated list 56 of likely malfunction areas.

The part description data in the first database 34 can be used to train the first classifier 42, and the data in the second database 38 can be used to train the second classifier 46. The third classifier 52 can be trained on predictions from the first and second classifiers 42, 46.

The first and second classifiers 42 and 46 can have a typical text classification structure, consisting of a pre-processing stage (e.g., input tokenization, removal of punctuation symbols etc.), vectorization stage, where tokens (e.g., words) are mapped to an m-dimensional vector space (e.g., TF-IDF, word2vec, etc.), and a machine learning-based classification stage (e.g., support vector machines). The output of each classifier 42 and 44 is an array of values between zero and one, with exactly one value assigned for each possible malfunction area. The lower (higher) the score the lesser (more) likely it is the maintenance case belongs to the corresponding malfunction area where values 0 and 1 are the lowest and highest possible values.

The third classifier 52 is programmed to combine the first and second classifiers 42 and 46 trained on different activity types. The third classifier 52, also known as stacked classifier, uses the predictions of the first classifier 42 and the second classifier 46 as input features (i.e., the scores per classifier per malfunction area), and has the same output type as the first classifier 42 and the second classifier 46. The implementation of the third classifier 52 can vary from simple (e.g., averaging, majority voting, and so forth) to more complex machine learning approach (e.g., linear regression, decision tree, and so forth).

In an example, the method 100 was used for a MR medical device 12. In MR, a malfunction area of a service case is determined based on the malfunction area of the most expensive part. The example focused on a set of 43,044 corrective maintenance cases from two countries, where 1,835 unique parts were replaced.

As noted, the first classifier 42 is generated for replacement parts of the medical device 12, and the second classifier 46 is generated for service cases to classify the malfunction area(s). Both classifiers 42, 46 have the same architecture, but are trained separately, do not share any internal state, and may learn different patterns.

Both classifiers 42, 46 can be trained and tested on the set of service cases/parts with a known malfunction area. To do so, a disjoint training/test split of the unique most expensive parts can be performed with 80% of parts in the training set, and 20% of the test set. This set was used for training and testing the second classifier 46. For creating the training and test set for the first classifier 42, services cases were assigned to the training/test set based on the assignment of their most expensive part in the first set.

Figure 3:
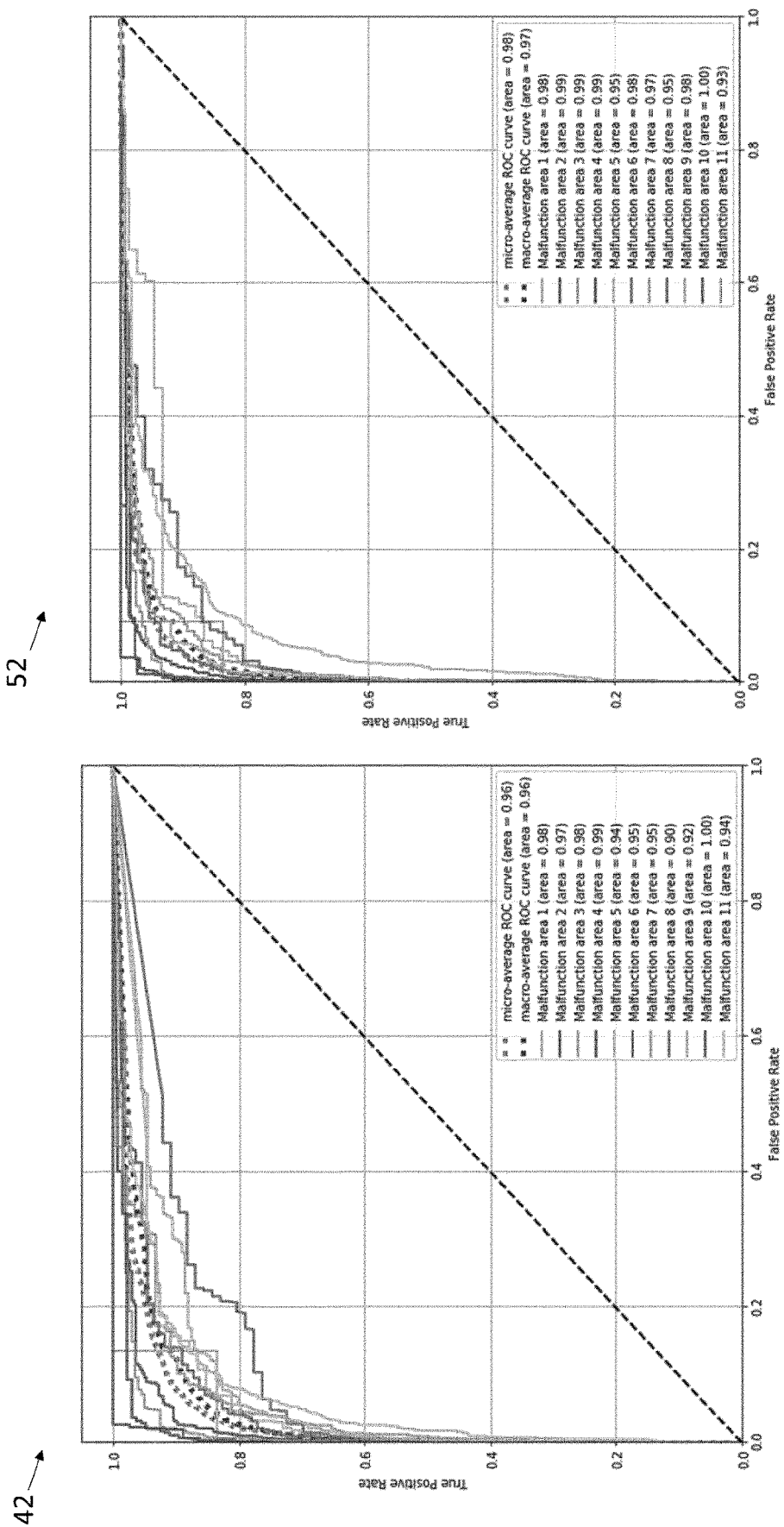
FIG. 3 shows a graph with data generated by the system of FIG. 1.

For the final list 56, the output vectors 44, 48 from the first and second classifiers 42, 46 can be combined. In some examples, the third output vector 54 can be combined with the output vectors 44, 48. The third classifier 52 can use, for example, a Logistic Regression process, as shown in the graph of FIG. 3. 错误!未找到引用源 shows the difference in performance between the first classifier 42, and the third classifier 46.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium storing instructions executable by at least one electronic processor to perform a method of automated identification of one or more malfunction areas of a set of malfunction areas for a service case in which a medical device is serviced, the method comprising:
   providing a parts ordering user interface for ordering parts for the service case, the parts ordering user interface providing text descriptions of parts ordered for the service case;
   providing a service report entry user interface for receiving a text description of the service case including at least a malfunction report for the medical device and repair notes for the service case;
   generating an output probability vector of probabilities for the set of malfunction areas of the medical device by operations including applying at least one classifier to at least one of (1) the text descriptions of the parts ordered for the service case and/or (2) the text description of the service case; and
   displaying a list of one or more probable malfunction areas for the service case wherein the one or more most probable malfunction areas are the one or more most malfunction areas of the set of malfunction areas having highest probability in the output probability vector.

2. The non-transitory computer readable medium of claim 1, wherein the generating of the output probability vector is by operations including applying a classifier to the text descriptions of the parts ordered for the service case.

3. The non-transitory computer readable medium of claim 1, wherein the generating of the output probability vector is by operations including applying a classifier to the text description of the service case.

4. The non-transitory computer readable medium of claim 1, wherein the generating of the output probability vector includes:
   generating a first probability vector of probabilities for the set of malfunction areas of the medical device by applying a first classifier to the text descriptions of the parts ordered for the service case;
   generating a second probability vector of probabilities for the set of malfunction areas of the medical device by applying a second classifier to the text description of the service case; and
   combining the first probability vector and the second probability vector to generate the output probability vector of probabilities of the one or more malfunction areas of the medical device.

5. The non-transitory computer readable medium of claim 4, wherein the method further includes:
   generating a third probability vector of probabilities for the set of malfunction areas of the medical device by applying a third classifier to data extracted from an automatically maintained machine log of the medical device;
   wherein the output probability vector is generated by combining the first probability vector, the second probability vector and the third probability vector.

6. The non-transitory computer readable medium of claim 1, wherein the at least one classifier comprises a support vector machine (SVM) classifier.

7. The non-transitory computer readable medium of claim 1, wherein, in the generating of the output probability vector, the text descriptions of the parts ordered for the service case and/or the text description of the service case are represented as a bag-of-words representation.

8. The non-transitory computer readable medium of claim 1, wherein the generating of the output probability vector and the displaying of the list are repeated iteratively to update the list in real-time as the parts ordering user interface receives orders for parts for the service case and/or the service report entry user interface receives updated repair notes for the service case.

9. The non-transitory computer readable medium of claim 1, wherein the method further comprises:
   receiving a user-identified malfunction area for the service case via a user input device interacting with the displayed list; and
   automatically adding the user-identified malfunction area to the text description of the service case.

10. The non-transitory computer readable medium of claim 1, wherein the parts ordering user interface provides for ordering parts for the service case from a parts inventory.

11. The non-transitory computer readable medium of claim 1, further storing instructions for recommending a repair action for the service case.

12. An apparatus for automated identification of one or more malfunction areas of a set of malfunction areas for a service case in which a medical device is serviced, the apparatus comprising:
   a server computer; and
   a non-transitory computer readable medium storing instructions executable by the server computer to perform a method including:
      providing a parts ordering user interface for ordering parts for the service case, the parts ordering user interface providing text descriptions of parts ordered for the service case;

providing a service report entry user interface for receiving a text description of the service case including at least a malfunction report for the medical device and repair notes for the service case;
generating a first probability vector of probabilities for the set of malfunction areas of the medical device by applying a first classifier to the text descriptions of the parts ordered for the service case;
generating a second probability vector of probabilities for the set of malfunction areas of the medical device by applying a second classifier to the text description of the service case;
combining the first probability vector and the second probability vector to generate an output probability vector probabilities of the one or more malfunction areas of the medical device; and
displaying a list of one or more probable malfunction areas for the service case wherein the one or more most probable malfunction areas are the one or more most malfunction areas of the set of malfunction areas having highest probability in the output probability vector.

13. The apparatus of claim 12, wherein the server computer is further programmed to:
generate a third probability vector of probabilities for the set of malfunction areas of the medical device by applying a third classifier to data extracted from an automatically maintained machine log of the medical device;
wherein the output probability is generated by combining the first probability vector, the second probability vector and the third probability vector.

14. The apparatus of claim 12, wherein the at least one first or second classifier comprises a support vector machine (SVM) classifier.

15. The apparatus of claim 12, wherein, in the generating of the output probability vector, the text descriptions of the parts ordered for the service case and/or the text description of the service case are represented as a bag-of-words representation.

16. The apparatus of claim 12, wherein the generating of the output probability vector and the displaying of the list are repeated iteratively to update the list in real-time as the parts ordering user interface receives orders for parts for the service case and/or the service report entry user interface receives updated repair notes for the service case.

17. The apparatus of claim 12, wherein the server computer is further programmed to:
receive a user-identified malfunction area for the service case via a user input device interacting with the displayed list; and
automatically add the user-identified malfunction area to the text description of the service case.

18. The apparatus of claim 12, wherein the parts ordering user interface provides for ordering parts for the service case from a parts inventory.

19. A method of automated identification of one or more malfunction areas of a set of malfunction areas for a service case in which a medical device is serviced, the method comprising:
providing a parts ordering user interface for ordering parts for the service case, the parts ordering user interface providing text descriptions of parts ordered for the service case;
providing a service report entry user interface for receiving a text description of the service case including at least a malfunction report for the medical device and repair notes for the service case;
generating an output probability vector of probabilities for the set of malfunction areas of the medical device by operations including applying at least one classifier to at least one of (1) the text descriptions of the parts ordered for the service case and/or (2) the text description of the service case;
displaying a list of one or more probable malfunction areas for the service case wherein the one or more most probable malfunction areas are the one or more most malfunction areas of the set of malfunction areas having highest probability in the output probability vector;
receiving a user-identified malfunction area for the service case via a user input device interacting with the displayed list; and
automatically adding the user-identified malfunction area to the text description of the service case.

20. The method of claim 19, wherein the generating of the output probability vector includes:
generating a first probability vector of probabilities for the set of malfunction areas of the medical device by applying a first classifier to the text descriptions of the parts ordered for the service case;
generating a second probability vector of probabilities for the set of malfunction areas of the medical device by applying a second classifier to the text description of the service case; and
combining the first probability vector and the second probability vector to generate the output probability vector of probabilities of the one or more malfunction areas of the medical device.

\* \* \* \* \*